United States Patent [19]

Weber, Jr.

[11] 4,307,720
[45] Dec. 29, 1981

[54] ELECTROCAUTERY APPARATUS AND METHOD AND MEANS FOR CLEANING THE SAME

[76] Inventor: Jaroy Weber, Jr., 2630 Bear Gulch Rd., Woodside, Calif. 94062

[21] Appl. No.: 61,020

[22] Filed: Jul. 26, 1979

[51] Int. Cl.³ .............................................. A61M 1/00
[52] U.S. Cl. .................................. 128/276; 128/305; 128/303.18
[58] Field of Search ............. 128/275.1, 276, 303.13, 128/303.14, 303.17, 303.18, 305; 30/162

[56] References Cited

U.S. PATENT DOCUMENTS

| | | | |
|---|---|---|---|
| 1,311,494 | 7/1919 | Camp | 128/303.18 |
| 2,710,000 | 6/1955 | Cromer et al. | 128/305 |
| 2,894,512 | 7/1959 | Tapper | 128/303.18 |
| 3,828,780 | 8/1974 | Morrison, Jr. | 128/275.1 |
| 3,884,237 | 5/1975 | O'Malley et al. | 128/303.14 |
| 3,906,955 | 9/1975 | Roberts | 128/275.1 |
| 3,974,833 | 8/1976 | Durden | 128/275.1 |
| 3,987,795 | 10/1976 | Morrison | 128/303.14 |
| 4,112,950 | 9/1978 | Pike | 128/303.14 |
| 4,137,920 | 2/1979 | Bonnet | 128/305 |

FOREIGN PATENT DOCUMENTS 2235669  1/1975  France ..................... 128/303.17

Primary Examiner—Robert W. Michell
Assistant Examiner—J. L. Kruter
Attorney, Agent, or Firm—A. C. Smith

[57] ABSTRACT

An improved electrocautery instrument includes a manually retractable-extendable electrode-blade with a vacuum channel disposed therebeneath. A guide in close-spaced relationship to the electrode-blade at the end of the instrument facilitates the scraping off and cleaning of the blade-electrode as it is retracted out of the way to configure the instrument for use as an uncluttered vacuum wand.

3 Claims, 3 Drawing Figures

ELECTROCAUTERY APPARATUS AND METHOD AND MEANS FOR CLEANING THE SAME

BACKGROUND OF THE INVENTION

Certain known electrocautery instruments for performing surgery with simultaneous hemostasis commonly become fouled with tissue and protein that adhere to the electrode. In order to maintain the efficient usefulness of such instruments throughout a surgical procedure, it is necessary to clean or replace the electrode frequently. In addition, it is usually desirable to have a suction port close to the tissue being cut and cauterized in order to remove the tissue rubble, blood, smoke and the like, that are present at the electrocautery site. And, it is usually desirable to perform the operations of electrocautery and evacuation of the site in selectable order rather than simultaneously. Devices which have these features are discussed in the literature (see, for example, U.S. Pat. Nos. 3,884,237, 3,906,955 and 3,828,780). However, these devices provide little or no control over the deployment of the electrode relative to the insulating handle in order to provide control of cutting and cauterization of tissue as well as to facilitate cleaning and evacuation of the operating site.

SUMMARY OF THE INVENTION

In accordance with the present invention, an improved electrocautery device includes manual control of the deployment of the electrode for cutting control as well as cleaning of the electrode. In retracted position, the electrode is out of the way for convenient use of the instrument as a vacuum wand for evacuating the operating site. In extended position, the electrode is cleaned off and ready for continued use in electrocautery procedures.

DESCRIPTION OF THE PREFERRED EMBODIMENT

Figure 1:
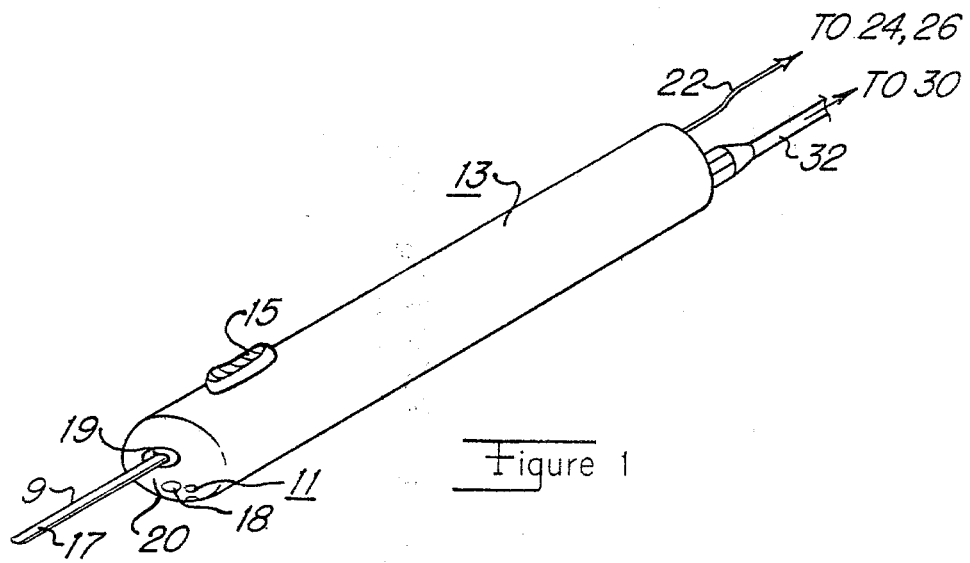
FIG. 1 is a perspective view of the electrocautery instrument of the present invention.
Figure 2:
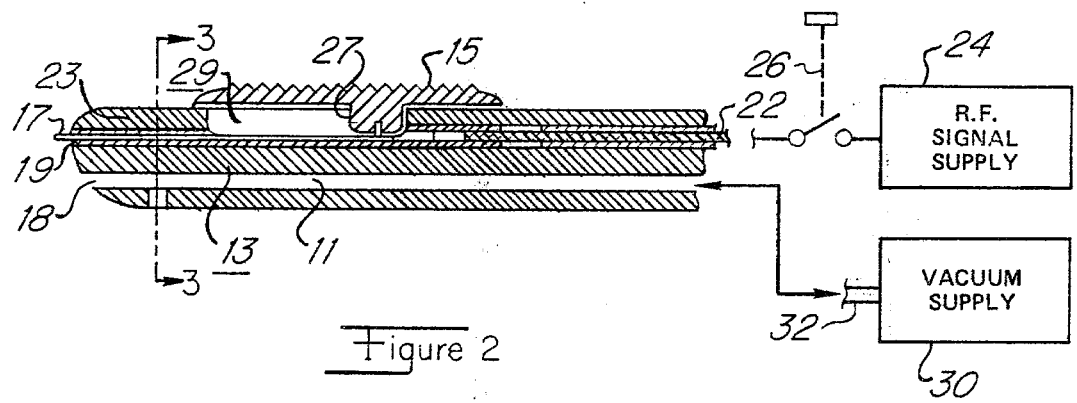
FIG. 2 is a side sectional view of the electrocautery instrument of FIG. 1.

Referring now to FIGS. 1 and 2, there are shown perspective and side sectional views of the electrocautery instrument of the present invention having an electrode 9 in the upper portion and a vacuum channel 11 in the lower portion. The body 13 of the instrument is conveniently shaped to rest in a surgeon's hand and includes a finger-actuated slide mechanism 15 for manually extending and retracting the electrode-blade 17. Extension and retraction of the electrode-blade 17 through guide 19 in slidable engagement therewith scrape off any adhering tissue debris, thus forcing such debris to accumulate at the tip 20 of the instrument where it can be wiped off merely by passing the tip 20 over sterilized gauze, or the like. Then, when desired, the electrode-blade 17 may again be extended by sliding the finger-actuated mechanism 15 forward to allow the cleaned electrode-blade 17 to protrude from the guide 19. The electrode-blade 17 is preferably wider than it is thick, as shown in FIGS. 1 and 2, to facilitate directional or slicing movement through tissue. Of course, the guide means, as referred to herein for the electrode-blade 17, may simply be a similarly-shaped aperture of the body at the forward end of the upper channel.

While the electrode-blade 17 is in the retracted position, the instrument is usable as an improved vacuum wand with a vacuum port 18 positioned in the lower, forward end of the instrument. With the electrode-blade 17 out of the way, there are no protrusions or obstructions on the forward end of the instrument to inhibit thorough evacuation of blood and tissue debris and smoke from the operating site. Further electrocautery procedures may then be pursued simply by extending the cleaned electrode-blade 17 through the guide 19.

The electrode-blade 17 is electrically connected via insulated wire 22 to a radio frequency (R.F.) signal source 24. A foot-operated switch 26 may be connected as shown to control the application of R.F. signal to the electrode-blade 17 or, more typically, may be connected to the supply 24 to enable and disable the R.F. generator so that R.F. signal is supplied or not supplied, respectively, to the electrode-blade 17. For convenience, the instrument may be made disposable and sterilized for one operation with a wire 22 attached to the blade support 23 that is free to slide in and out of the guide 19 in body 13 as the blade 17, which is attached to the blade support 23, is retracted and extended. Alternatively, the electrode-blade 17 may simply be a flattened, forward portion of the blade support 23 that is free to slide within the guide 19 which is correspondingly flattened at the forward end thereof, as shown. The finger-actuated mechanism 15 may include an integral protrusion 27 which snaps down over a pin in the support 23 to complete the assembly. The body 13 and mechanism 15 may be made of biologically-inert plastic such as TEFLON (trademark of DuPont Company) or other suitable dielectric material which can insulate the electrical circuitry from the surgeon's hand and which can be sterilized after manufacture. The protrusion 27 that couples the mechanism 15 to the support 23 slides in a longitudinal slot 29 within body 13 and the mechanism 15 provides electrical insulation over the slot to protect the surgeon's finger from R.F. signal present on the guide 19, support 23 and blade 17.

Figure 3:
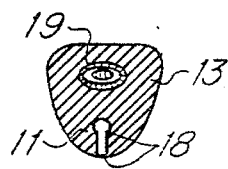
FIG. 3 is an end sectional view of the electrocautery instrument of FIG. 1.

The vacuum channel 11 in the lower portion of the body 13 is connected to a vacuum supply 30 via flexible conduit or tube 32. The inlet port 18, as shown in FIGS. 1, 2 and 3, may include openings that are directed forwardly, sidewardly and downwardly to facilitate the convenient evacuation of an operating site.

I claim:
1. A surgical instrument comprising:
an elongated body having upper and lower channels extending therethrough, the lower channel serving as a vacuum conduit with a vacuum port therefor disposed at the forward, lower end of the body;
guide means disposed in the upper channel near the forward, upper end of the body;
an electrode-blade disposed within the upper channel and slidably extendable through the guide means to selectably protrude from the forward end of the body;
slider means coupled to and electrically insulated from the electrode-blade and manually operable exteriorly of the body for selectably extending and retracting the electrode-blade through the guide means between completely retracted and extended positions; and means for coupling radio frequency signal to the electrode-blade, said electrode-blade is wider than it is thick;

and said guide means is positioned about the electrode-blade in close-spaced, slidable engagement therewith to facilitate the scraping off of any debris adhering to the electrode-blade slidably retracted through the guide means.

2. Electrocautery apparatus comprising:

an elongated body having guide means longitudinally disposed within the body;

an electrode slidably mounted within the guide means for selectably extending and retracting through the forward end of the body;

slider means coupled to and electrically insulated from the electrode and manually operable exteriorly of the body for selectably extending and retracting the electrode through the forward end of the body between completely retracted and extended positions, and means coupling radio frequency signal to the electrode, said guide means is disposed in close-fitting, slidable engagement about the electrode near the forward end of the body for scraping adherent debris from the electrode in response to manual retraction of the electrode.

3. The method of cleaning an electrocautery apparatus having an electrode protruding from the forward end thereof, comprising the steps of:

slidably mounting the electrode within the apparatus;

slidably retracting the electrode into the apparatus through the forward end thereof for scraping adherent debris from the electrode thereof under manual operation applied exteriorly of the apparatus; and guiding the slidably-retracting movement of the electrode with close-spaced sliding engagement therewith at the forward end of the apparatus to scrape adherent debris from the electrode.

* * * * *